United States Patent
Amland et al.

(10) Patent No.: US 8,751,257 B2
(45) Date of Patent: Jun. 10, 2014

(54) READMISSION RISK ASSESSMENT

(75) Inventors: Robert Charles Amland, Lenexa, KS (US); Hugh Ryan, Lee's Summit, MO (US); Jason Howard, Lee's Summit, MO (US); Bharat Sutariya, Parkville, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 12/817,602

(22) Filed: Jun. 17, 2010

(65) Prior Publication Data

US 2011/0313788 A1    Dec. 22, 2011

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | |
|---|---|---|
| 2005/0216312 A1 | 9/2005 | Bellin et al. |
| 2005/0222867 A1* | 10/2005 | Underwood et al. ............. 705/2 |
| 2011/0246220 A1* | 10/2011 | Albert ............................... 705/2 |
| 2012/0004925 A1 | 1/2012 | Braverman et al. |

OTHER PUBLICATIONS

Notice of Allowance and Fee(s) Due in U.S. Appl. No. 13/284,088, mailed Oct. 7, 2013, 25 pages.
PreInterview First Action Interview in U.S. Appl. No. 13/284,088, mailed Sep. 4, 2013, 9 pages.
Perez-Valdivieso, et al., "Cardiac-surgery associated acute kidney injury requiring renal replacement therapy. A Spanish retrospective case-cohort study", BMC Nephrology 2009, www.biomedcentral. com/1471-2369/10/27.
Justice, Amy C., et al. "Assessing the Generalizability of Prognostic Information", Ann Intern Med.1999;130:515-524., 1999 American College of Physicians-American Society of Internal Medicine.

* cited by examiner

*Primary Examiner* — Robert Morgan
*Assistant Examiner* — Maroun Kanaan
(74) *Attorney, Agent, or Firm* — Shook Hardy & Bacon LLP

(57) ABSTRACT

A readmission risk prediction model is generated and used for identifying patients having elevated risk of readmission and determining inpatient treatment and outpatient activities based on readmission risk. Readmission risk prediction models may be generated for a variety of different clinical conditions using logistic regression techniques. When a patient is admitted to a hospital, the patient's condition is identified and a corresponding readmission risk prediction model is employed to identify the patient's risk of readmission. The readmission risk may be presented to a clinician and employed to recommend interventions intended to treat the patient and reduce the probability of readmission for the patient. The patient's readmission risk may also be calculated after the patient has been discharged and used for planning outpatient activities for the patient.

19 Claims, 9 Drawing Sheets

| HEART FAILURE OUTPATIENT SURVEILLANCE | ☐ CALL | ☐ NO CALL | | | | HIGH RISK INPATIENTS | |
|---|---|---|---|---|---|---|---|
| PATIENT NAME | AGE | PHONE # | DISCHARGE DAYS | LAST CONTACTED | FOLLOW-UP VISIT | | VISIT COMPLETE? |
| + ADAMS, JOHN | 45 | 816-555-1234 | 1 | N/A | THUR 01/28 | | N/A |
| + ARTHUR, CHESTER | 61 | 816-555-1235 | 30 | FRI 01/02 | WED 12/30 | | YES |
| + BUCHANAN, JAMES | 48 | 816-555-1236 | 5 | FRI 01/22 | MON 01/25 | | ? |
| + BUSH, GEORGE | 55 | 816-555-1237 | 14 | WED 01/20 | MON 01/18 | | YES |
| + CARTER, JIMMY | 60 | 816-555-1238 | 12 | MON 01/25 | TUES 01/19 | | NO |
| + CLEVELAND, GROVER | 55 | 816-555-1239 | 10 | FRI 01/22 | WED 01/20 | | YES |
| + PATIENT, JOE | 55 | 816-555-1240 | 10 | FRI 01/22 | THRU 01/21 | | YES |

READMISSION RISK ASSESSMENT

BACKGROUND

An unplanned readmission occurs when a patient is readmitted to a hospital within a certain period of time (e.g., 30 days) after having been discharged from the hospital for treatment of the same or related condition. Readmission rates are particularly high with certain conditions, such as heart failure and pneumonia. Hospitals are typically concerned with reducing the number of unplanned readmissions as they may reflect upon the quality of treatment provided by the hospitals and also result in significantly increased costs. Often, readmissions may have been preventable if the patients received proper care while admitted at the hospitals during the first visit and/or if the patients' length of stay had been extended. Additionally, readmissions may have been preventable if proper monitoring and education had been provided to patients after discharge. However, it is typically difficult to identify the proper inpatient treatments and post-discharge care appropriate for properly treating patients and preventing readmissions.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to generating readmission risk prediction models for determining the risk of readmission for patients and using the patients' readmission risk in determining proper inpatient interventions and/or outpatient activities. Readmission risk prediction models may be generated using linear regression techniques over clinically relevant data for any of a variety of different clinical conditions. In embodiments, a readmission risk prediction model may be built around a single patient condition or multiple patient conditions. When a patient is admitted to a hospital or other clinical facility, the patient's condition is identified and a corresponding readmission risk prediction model is used to determine the patient's readmission risk. Inpatient treatment interventions may be identified based on the patient's readmission risk and provided as clinical decision support to a clinician. Additionally, the patient's readmission risk may be reassessed and the patient's care plan adjusted over the patient's stay. When the patient is discharged, the patient's readmission risk score may be used to identify outpatient activities for the patient. Further, the patient's readmission risk may be reassessed after the patient has been discharged and the post-discharge readmission risk may be used for determining outpatient activities and/or to readmit the patient.

Accordingly, in one aspect, an embodiment of the present invention is directed to one or more computer storage media storing computer-useable instructions that, when used by one or more computing devices, cause the one or more computing devices to perform a method. The method includes identifying a patient condition for a patient admitted to a clinical facility and selecting a readmission risk prediction model based on the patient condition. The method also includes receiving patient data for the patient and computing a readmission risk score using the readmission risk prediction model and the patient data, the readmission risk score representing a probability of readmission for the patient. The method further includes providing an indication of readmission risk for the patient based on the readmission risk score for presentation to a clinician treating the patient.

In another embodiment, an aspect of the invention is directed to one or more computer storage media storing computer-useable instructions that, when used by one or more computing devices, cause the one or more computing devices to perform a method. The method includes computing a readmission risk score for a patient previously discharged from a clinical facility. The method also includes determining an outpatient treatment recommendation based on the readmission risk score. The method further includes providing the outpatient treatment recommendation for presentation to a clinician.

A further embodiment of the present invention is directed to one or more computer storage media storing computer-useable instructions that, when used by one or more computing devices, cause the one or more computing devices to perform a method. The method includes receiving clinically relevant data associated with a given clinical condition from a plurality of patient cases. The method also includes building a logistic regression model using the clinically relevant data. The method further includes developing a readmission risk prediction model using the logistic regression model, the readmission risk prediction model being capable of calculating a readmission risk score for patients based on patient data, wherein a readmission risk score for a patient represents a probability of readmission for the patient.

BRIEF DESCRIPTION OF THE DRAWINGS

The present invention is described in detail below with reference to the attached drawing figures, wherein:

FIG. 6 is a screen display of an exemplary view illustrating an outpatient surveillance call list in accordance with an embodiment of the present invention;

FIG. 8 is a screen display of an exemplary view illustrating a user interface for tracking outpatient information in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems for generating readmission risk prediction models using linear regression techniques. Embodiments of the present invention further provide computerized methods and systems for employing the readmission risk prediction models to assess the readmission risk of patients and determine inpatient treatment interventions and outpatient activities based on the patients' readmission risk. An exemplary operating environment is described below.

Figure 1:
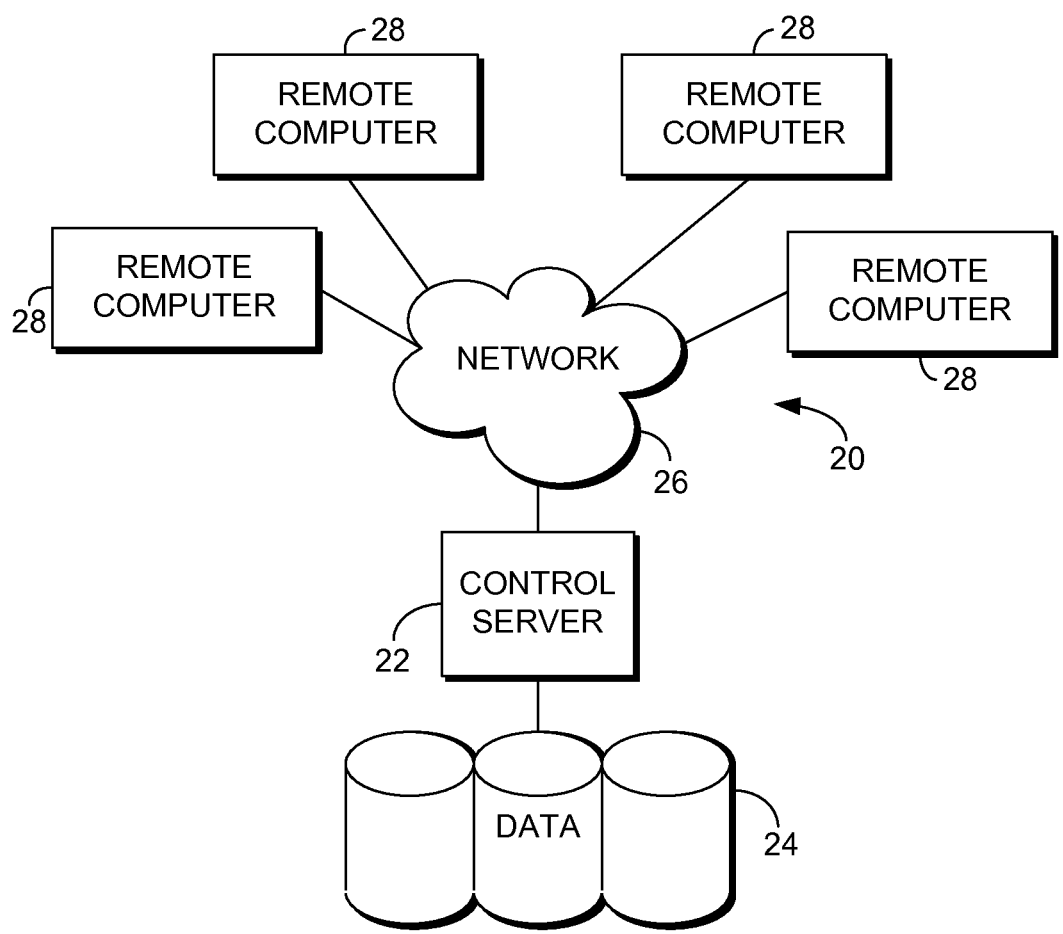
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

As previously mentioned, embodiments of the present invention relate to generating readmission risk prediction models and using the readmission risk prediction models to facilitate inpatient treatment and/or outpatient activities. In embodiments, readmission risk prediction models may be generated utilizing logistic regression of existing clinically relevant data. Each readmission risk prediction model may be generated for a given condition using clinically relevant data from patients diagnosed with that condition. Additionally, in some embodiments, a readmission risk prediction model may be built around multiple conditions.

The readmission risk prediction models may be embedded within electronic medical systems or provided as a standalone software tool that facilitates determining the readmission risk of patients. In accordance with embodiments of the present invention, when a patient is admitted to a hospital or other clinical facility, the patient's condition may be diagnosed. Based on the patient's condition, a readmission risk prediction model may be selected and used to calculate a readmission risk score that represents the probability of readmission for the patient. The readmission risk may be based on readmission within a predetermined period of time, such as within 7 days after discharge, within 30 days after discharge, within 60 days after discharge, within 90 days after discharge, etc.

The readmission risk determined for patients may be utilized during hospitalization to drive clinical workflows for the patients. This may include linking the readmission risk for patients to clinical decision support and providing user interfaces to assist in identifying interventions for patients and also linking to orders to allow clinicians to enter orders based on review of readmission risk. For instance, readmission risk scores may help identify high readmission risk patients such that clinicians may determine proper interventions for those patients. In some embodiments, the system may recommend treatment interventions based on patients' readmission risks. For instance, readmission risk may be used to modify a patient's care plan including recommending alternate therapies, performing additional studies, and/or extending the patient's length of stay. Additionally, the readmission risk may be linked to clinical decision support and/or order subsystems such that clinicians may be identify and implement patient treatments deemed appropriate based in part on patients' readmission risks. In some embodiments, readmission risk scores may be recalculated over the length of hospitalization for patients and the patient care plans modified based on the recalculated readmission risk scores.

In addition to facilitating inpatient treatment, readmission risk may be used to facilitate discharge planning and outpatient activities. For instance, readmission risk may be used to determine the need for and scheduling of surveillance calls to patients and/or in-person appointments, in-home treatment, and patient education. In some embodiments, readmission risk scores may also be calculated after a patient has been discharged. Such post-discharge readmission risk scores may be used to modify outpatient activities and may warrant readmitting patients in some instances.

Figure 2:
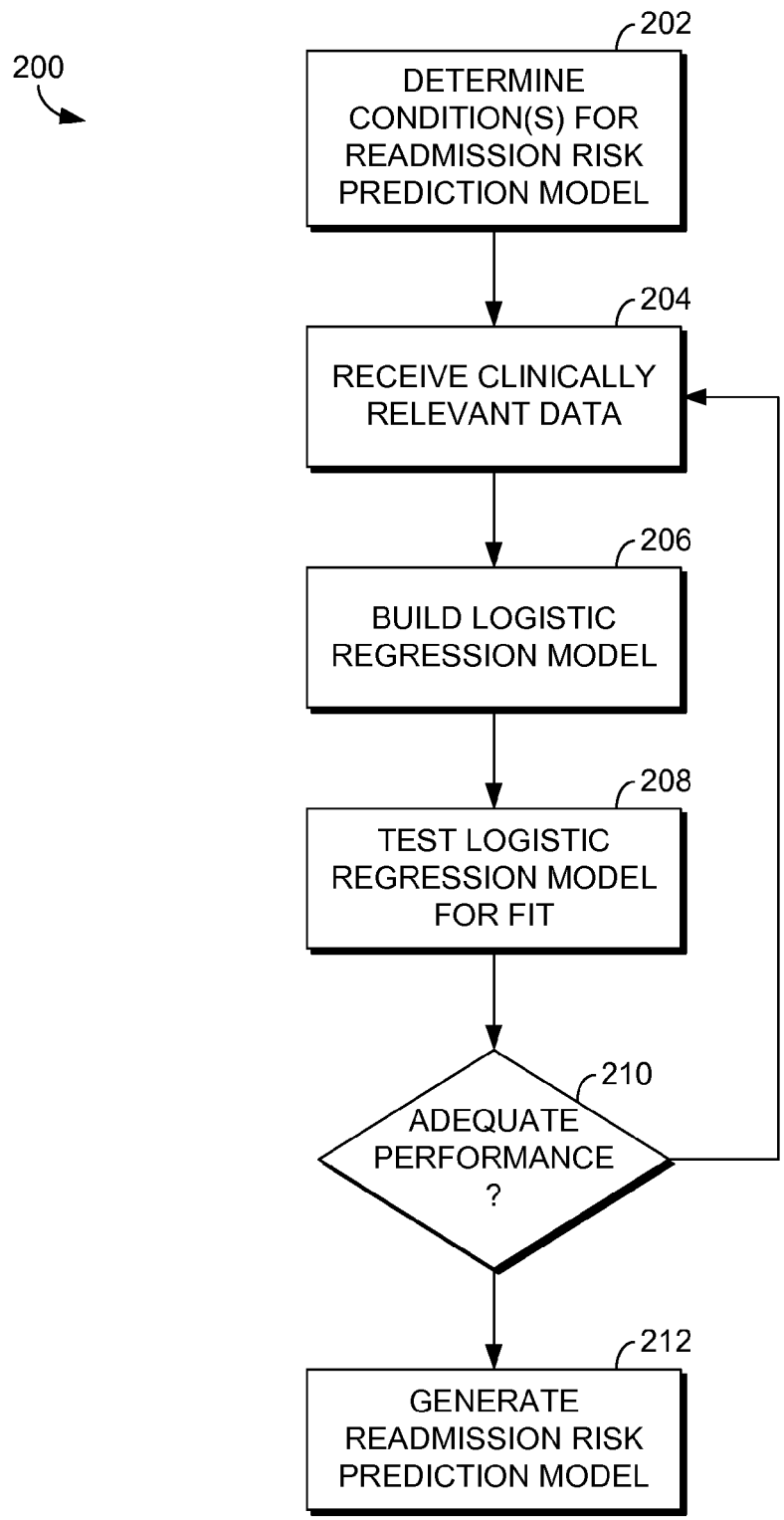
FIG. 2 is a flow diagram showing a method for generating a readmission risk prediction model in accordance with an embodiment of the present invention.

Referring now to FIG. 2, a flow diagram is provided that illustrates a method 200 for generating a readmission risk prediction model in accordance with an embodiment of the present invention. Initially, the condition around which the readmission risk prediction model will be generated is determined, as shown at block 202. As indicated previously, risk prediction models may be built around any given condition. For instance, a risk prediction model may be built around heart failure, acute myocardial infarction, pneumonia, acute kidney injury, sepsis, to name a few. In some embodiments, a readmission risk prediction model may be built around multiple conditions, each of which is identified at block 202.

Clinically relevant data for the identified condition is accessed at block 204 for use as training data. The clinically relevant data may come from any of a variety of public or private sources, including, for instance, hospital electronic medical records, research facilities, and academic institutions. The data may be collected manually or may be retrieved using electronic data gathering mechanisms. In embodiments, the process may include identifying relevant cases useful for constructing a readmission risk prediction model for the condition identified at block 202. Additionally, the process may include identifying input and output variables relevant to the identified condition. In some embodiments, evidence-based practices may be used in determining relevant cases and variables.

As shown at block 206, a logistic regression model is built using the retrieved clinically relevant data. In embodiments, the logistic regression model may be built around patient readmissions within one or more given time periods, such as readmission within 7 days after discharge, within 30 days after discharge, within 60 days after discharge, within 90 days after discharge, etc. The logistic regression model is then tested for model fit, as shown at block 208. This may include performing analyses to determine how well the model predicts outcomes, how well the model calibrates, and whether the model is clinically useful. By way of example only, the model may be tested by performing a receiver-operating characteristic (ROC) area-under-the-curve (C-statistic) analysis to determine how well the model predicts outcomes. As another example, the model may be analyzed using a chi-square test to determine how well the model calibrates.

Whether the performance of the logistic regression model is adequate based on the model testing is determined at block 210. If the performance of the logistic regression model is deemed to be inadequate, the process of selecting clinically relevant data and/or building a logistic regression model may be iterated until sufficient performance is achieved. A readmission risk prediction model is then generated using the output from the logistic regression model, as shown at block 212.

Figure 3A:
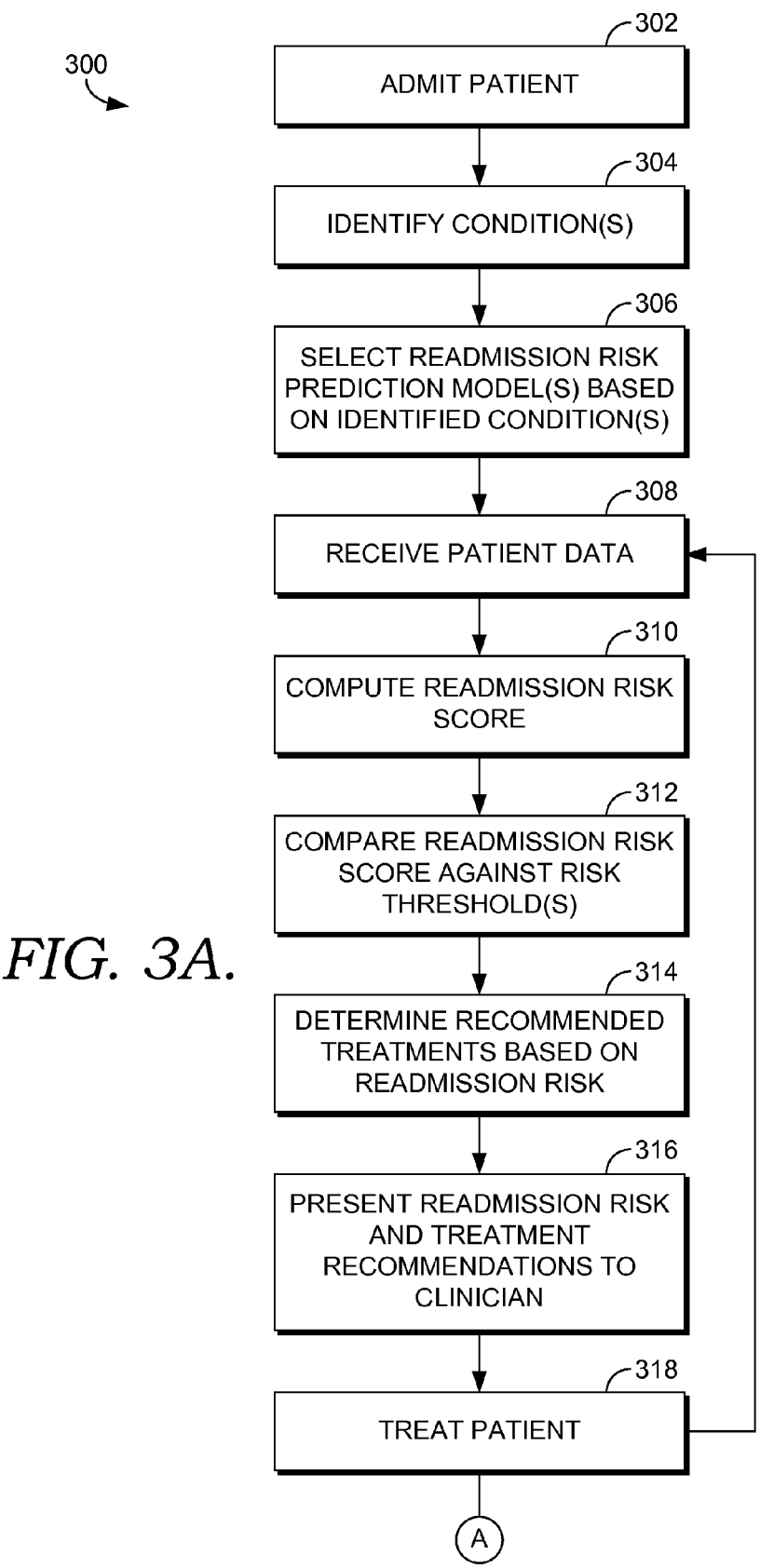
FIGS. 3A and 3B include a flow diagram showing a method for using readmission risk for inpatient treatment and outpatient activity planning in accordance with an embodiment of the present invention.
Figure 3B:
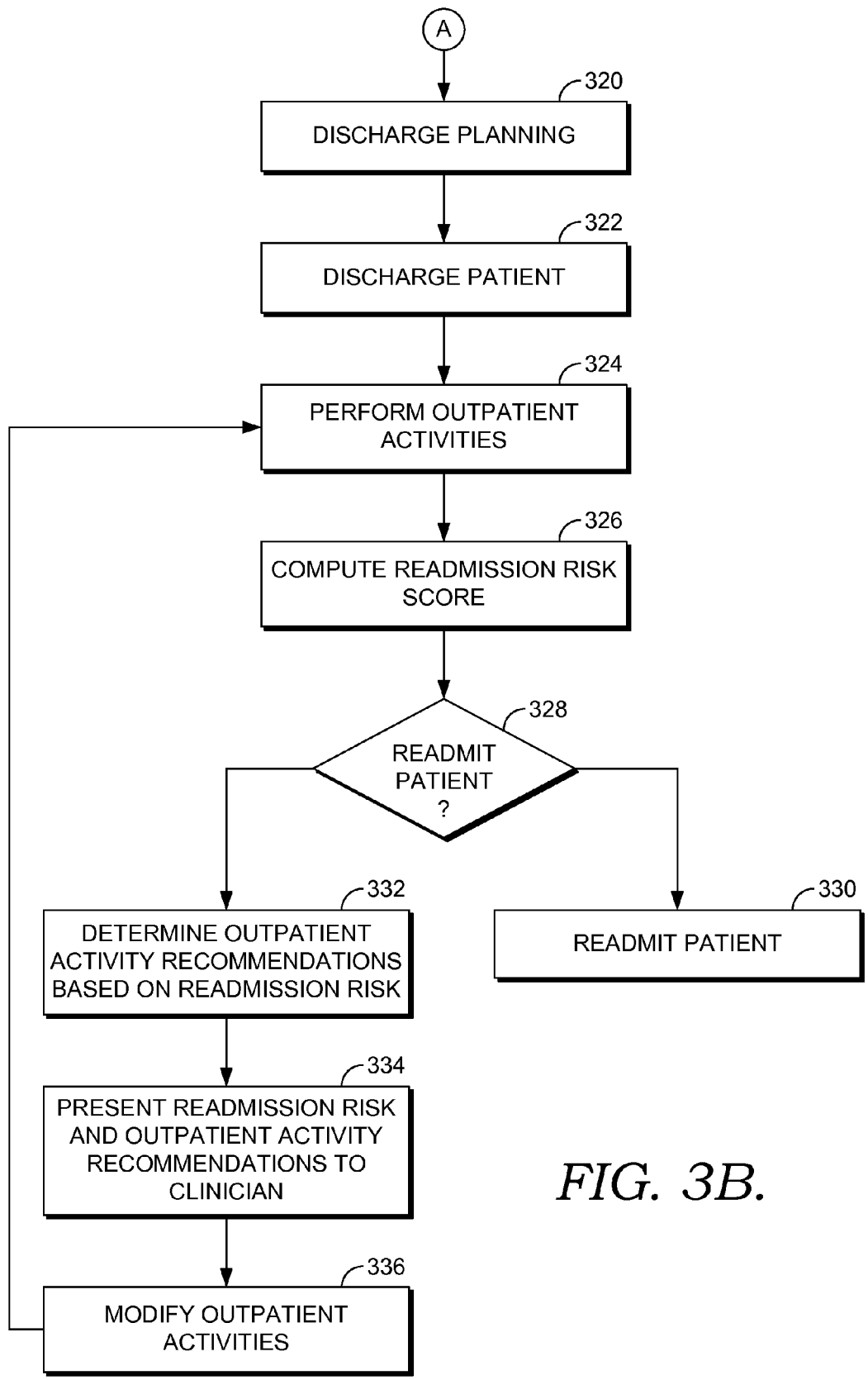

Turning next to FIGS. 3A and 3B, a flow diagram is provided that illustrates a method 300 for using a readmission risk score to facilitate treatment of a patient in accordance with an embodiment of the present invention. Initially, as shown at block 302, a patient is admitted to a hospital or other clinical facility. Upon admitting the patient, a condition is identified for the patient, as shown at block 304. In some instances, the patient may be suffering from a single condition and the single condition is identified, while in other instances, the patient may be suffering from multiple conditions and the multiple conditions are identified at block 304.

A readmission risk prediction model is selected at block 306 based on the condition identified for the patient at block 304. In instances in which a single condition is identified, a readmission risk prediction model corresponding with that condition is selected. For instance, if the patient is identified as suffering from heart failure, the system selects a readmission risk prediction model that was built around heart failure patients to determine the readmission risk of heart failure patients. In some embodiment in which multiple conditions are identified for the patient, a single readmission risk prediction model built around those identified conditions is selected. For instance, a patient may be suffering from heart failure and pneumonia, and a single readmission risk prediction model built around those two conditions may be selected. In other embodiments in which multiple conditions are identified, multiple readmission risk prediction models are selected, each model corresponding with one of the identified conditions. For instance, if the patient is suffering from heart failure and pneumonia, a readmission risk prediction model for heart failure and a readmission risk prediction model for pneumonia may both be selected and used in conjunction to identify readmission risk for the patient.

Patient data for the patient is received at block 308. The patient data may include demographic data and/or clinically relevant data for the patient. Additionally, the data received at block 308 may be dependent upon the selected readmission risk prediction model. In particular, each readmission risk prediction model may have a number of input variables that are relevant to that model. As such, data corresponding with the relevant variables are received as input to the model for readmission risk assessment purposes.

In some embodiments, the readmission risk prediction models may be embedded within an electronic medical system that includes electronic medical records or otherwise may be in communication with electronic medical records for patients. In such embodiments, the patient data may be received by accessing the electronic medical record for the patient and retrieving the relevant data. In some instances, patient data used by the readmission risk prediction model may not be available in the patient's electronic medical records, and the system may prompt a clinician to enter the data or to order particular tests to be performed to obtain the data. In further embodiments, the readmission risk prediction models may be provided in standalone software separate from an electronic medical record, and a clinician may enter the patient data as variables for the readmission risk prediction model. Any and all variations are contemplated to be within the scope of embodiments of the present invention.

A readmission risk score is computed using the selected readmission risk prediction model and the received patient data, as shown at block 310. The readmission risk score is then compared against one or more thresholds, as shown at block 312. In accordance with embodiments of the present invention, thresholds may be set by the clinical facility treating the patient, an external policy maker, and/or other entity and used to trigger treatment recommendations based on the risk of readmission. The thresholds may be condition-specific. For instance, a readmission risk threshold used for heart failure patients may differ from a readmission risk threshold used for pneumonia patients.

In some embodiments, a single threshold may be provided. If the readmission risk score exceeds the threshold, the patient is identified as a high risk for readmission. Alternatively, if the readmission risk score is below the threshold, the patient is considered to be a low readmission risk. In other embodiments, multiple thresholds may be set providing more than two ranges of readmission risk scores corresponding with more than two levels of readmission risk.

As shown at block 314, treatment recommendations are determined based on the patient's readmission risk level. The treatment recommendations may be any of a variety of different interventions intended to treat the patient's condition and reduce the likelihood that the patient would need to be readmitted. For instance, as noted above, a single threshold may be used such that the readmission risk score indicates either a low or high readmission risk. In some embodiments, if the readmission risk is low, no interventions may be recommended and the care plan may remain unmodified. Alternatively, if the threshold is exceeded such that the readmission risk is high, certain interventions or a modified care plan may be recommended based on the high readmission risk. In embodiments in which multiple thresholds are used providing multiple risk levels, treatment recommendations may be determined based on the risk level determined for the patient. In various embodiments of the present invention, the treatment recommendations may be predetermined for each risk level or the system may analyze or provide tools that allow a clinician to analyze the input variables used by the readmission risk prediction model to identify personalized treatment recommendations for the patient.

The readmission risk and/or recommended treatments for the patient are presented to a clinician, as shown at block 316. The readmission risk may be presented, for instance, as a readmission risk score comprising a percentage indicating the probability that the patient will need to be readmitted after discharge. In addition to or in lieu of presenting a readmission risk score, the readmission risk determined by comparison to one or more thresholds may be presented to a clinician. For example, the patient may be identified as a high readmission risk. As noted above, in some embodiments, the system may automatically recommended interventions based on the readmission risk level, and the system may present those interventions. In other embodiments, after determining that the readmission risk score exceeds certain thresholds, the system may provide tools to the clinician to allow the clinician to explore reasons why the readmission risk score is high and to determine the best treatment options for the patient.

In some embodiments, the readmission risk score and recommended treatments may only be presented if a threshold is exceeded by the patient's readmission risk score. For instance, if the patient's readmission risk score is low, no readmission risk information may be presented to the clinician and a routine care plan may be provided. In other embodiments, the system may provide an indication to the clinician that the readmission risk for the patient is low.

Treatment alternatives are selected, and the patient is treated, as shown at block 318. This may include performing a routine care plan if the readmission risk is low or performing a modified care plan including interventions recommended based on readmission risk exceeding certain thresholds. While the patient is treated, the readmission risk score may be recalculated as shown by the return to block 308. The readmission risk score may be recalculated at predetermined points in time or any time patient data is updated that may impact the readmission risk score for the patient. Based on the readmission risk score recalculations, different treatments options may be recommended and/or the patient's care plan may be modified. As such, the patient's readmission risk may be monitored during treatment and the patient's care modified as dictated by the patient's readmission risk.

In some embodiments, the system may monitor risk score trending for the patient during treatment and use such trending information to provide treatment recommendations. For instance, multiple readmission risk score calculations may indicate that the patient's readmission risk is decreasing, demonstrating that the current care plan is effective. Alternatively, readmission risk score trending may correspond with the patient's readmission risk remaining stable or even increasing, demonstrating that the current care plan is ineffective and/or that different interventions may be necessary.

After treating the patient, discharge planning is conducted prior to discharging the patient, as shown at block 320. This may include recalculating a readmission risk score for discharge planning purposes and/or using a previously obtained readmission risk score or risk score trending in discharge planning. In some embodiments, the patient's readmission risk score may be used to determine whether to discharge the patient. For instance, a rule may dictate that the patient may not be discharged until the patient's readmission risk score falls below a certain threshold or exhibits a certain downward trend over time.

Discharge planning may also include planning outpatient activities to be conducted after the patient is discharged. In embodiments, the patient's readmission risk score may be used in planning the outpatient activities for the patient. The outpatient activities may include performing patient monitoring, such as outpatient surveillance calls from a clinician to the patient, scheduling appointments for the patient, providing in-home healthcare, and educating the patient on healthcare issues related to the patient's condition. The patient's readmission risk score may be used to determine which outpatient activities to provide for the patient and may also determine a schedule for surveillance calls and/or appointments. For instance, if the patient is determined to be a high risk for readmission, the discharge planning may include placing the patient on a surveillance call list for high risk patients.

After discharge planning is performed, the patient is discharged, as shown at block 322. Any outpatient activities planned by the patient are performed after discharge, as shown at block 324. As noted above, the outpatient activities may include surveillance calls, appointments, as well as a number of other activities. Additionally, the patient's readmission risk score is calculated after the patient has been discharged, as shown at block 326. The readmission risk score may be calculated, for instance, based on additional information gathered from patient calls and appointments.

The readmission risk score calculated for a patient after discharge may be used for a number of purposes, such as determining whether to readmit the patient and whether to alter the patient's outpatient activities. Accordingly, as shown at block 328, a determination is made regarding whether to readmit the patient based on the readmission risk score calculated at block 326. This determination may be made, for instance, by comparing the readmission risk score to a threshold and determining to readmit based on the readmission risk score exceeding the threshold. The determination may also be made on readmission risk trending demonstrating a certain increase in readmission risk over time. The determination to readmit the patient may be based on clinician judgment as well. For instance, the system may present a notice to the clinician recommending that the patient be readmitted based on the readmission risk score and the clinician may review the notice and determine whether to readmit the patient. If it is determined that the patient should be readmitted, the patient may be readmitted as shown at block 330. If readmitted, the patient may be treated and the patient's readmission risk tracked and used for treatment purposes as described above.

Alternatively, it may be determined that the patient should not be readmitted at block 328. For instance, the patient's risk score may not exceed a predetermined threshold and/or a treating clinician may determine not to readmit. However, it may be desirable to modify the outpatient activities for the patient based on the readmission risk score. For instance, more frequent monitoring or additional testing may be desirable based on an elevated readmission risk score. As another example, no further outpatient activities may be deemed advisable based on a decreased readmission risk. Accordingly, as shown at block 332, outpatient activity recommendations are determined based on the outpatient readmission risk score. The readmission risk and/or outpatient activity recommendations are presented to a clinician, as shown at block 334. Based on the readmission risk and/or recommendations, the outpatient activities may be modified, as shown at block 336. The process of performing outpatient activities and recalculating readmission risk may be repeated until the patient is readmitted or until it is determined that outpatient activities and readmission risk score monitoring is no longer necessary.

As discussed previously, embodiments of the present invention include providing graphical user interfaces that facilitate inpatient treatment and outpatient activities based on readmission risk. FIGS. 4 through 8 are illustrative of user interfaces providing readmission risk information for patients and proving clinical decision support to clinicians based on readmission risk. It will be understood and appreciated by those of ordinary skill in the art that the screen displays of FIGS. 4 through 8 are provided by way of example only and are not intended to limit the scope of the present invention in any way.

Figure 4:
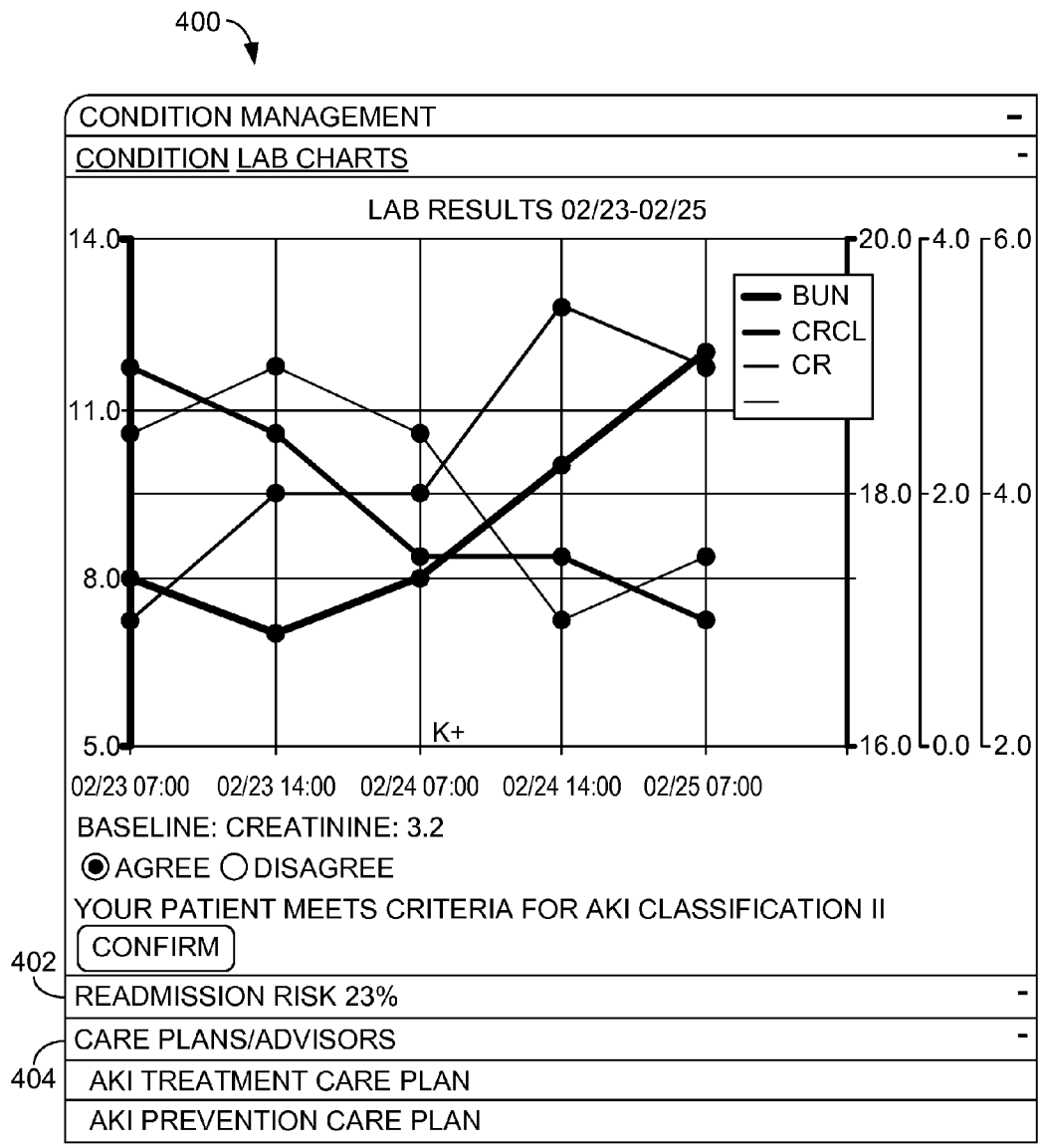
FIG. 4 is a screen display of an exemplary view illustrating condition management for a patient including lab results for the patient and the patient's readmission risk in accordance with an embodiment of the present invention.

Referring initially to FIG. 4, an illustrative screen display 400 is provided showing readmission risk in context of a condition management view for a patient in accordance with an embodiment of the present invention. The condition management view provides lab results information for the patient. Additionally, the condition management view provides an indication of readmission risk 402 for the patient. The condition management view further includes clinical decision support 404 in the form of care plans that are suggested by the system based on the patient's readmission risk. The clinician may review the information, including the patient's readmission risk, and determine whether to implement suggested care plans.

Figure 5:
FIG. 5 is a screen display of an exemplary view illustrating a user interface for generating orders for patients including a initiating a readmission risk protocol in accordance with an embodiment of the present invention.

Turning to FIG. 5, an illustrative screen display 500 is provided that shows a user interface allowing a clinician to enter orders for a patient in accordance with an embodiment of the present invention. As shown in FIG. 5, the orders user interface allows the clinician to select from a number of different orders. The orders user interface also provides an indication: "This patient meets criteria for 'High' 30 day readmission risk" and suggests that the clinician initiate a heart failure readmission risk protocol. Accordingly, the clinician can review the information and understand that the patient has been identified as a high readmission risk. Based on this information, the clinician may select an order 502 to implement the heart failure readmission risk protocol for the patient.

As noted above, in addition to providing inpatient treatment tools, some embodiments of the present invention may provide tools facilitating outpatient activities for patients after discharge from a hospital. FIG. 6 provides an illustrative screen display 600 of an outpatient surveillance user interface in accordance with an embodiment of the present invention. The outpatient surveillance user interface may include two lists of patients: patients on a call list and patients on a no call list. A clinician may toggle between the two lists using the links 602 and 604. In some embodiments, patients having a high readmission risk may be placed on the call list while patients having a low readmission risk may be placed on the no call list. Patients may be moved from one list to another based on readmission risk and clinician judgment.

The screen display 600 illustrates a view of the patient call list. The list may be used to by clinicians to manage outpatient surveillance calls to patients. The list may include information such as contact information for each patient, how long ago each patient was discharged, when each patient was previously contacted, scheduled contact for each patient, etc.

Figure 7:
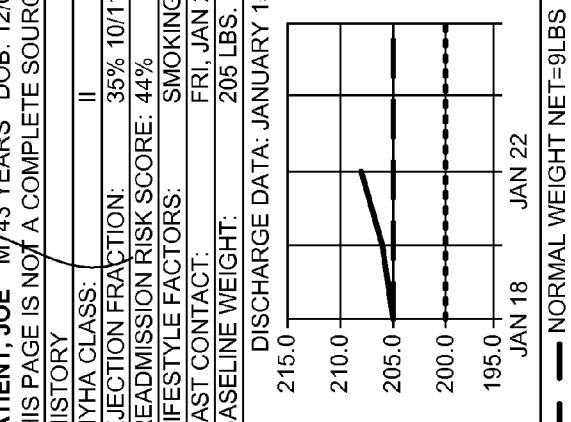
FIG. 7 is a screen display of an exemplary view illustrating patient summary information for managing an outpatient call in accordance with an embodiment of the present invention.
Figure 8:
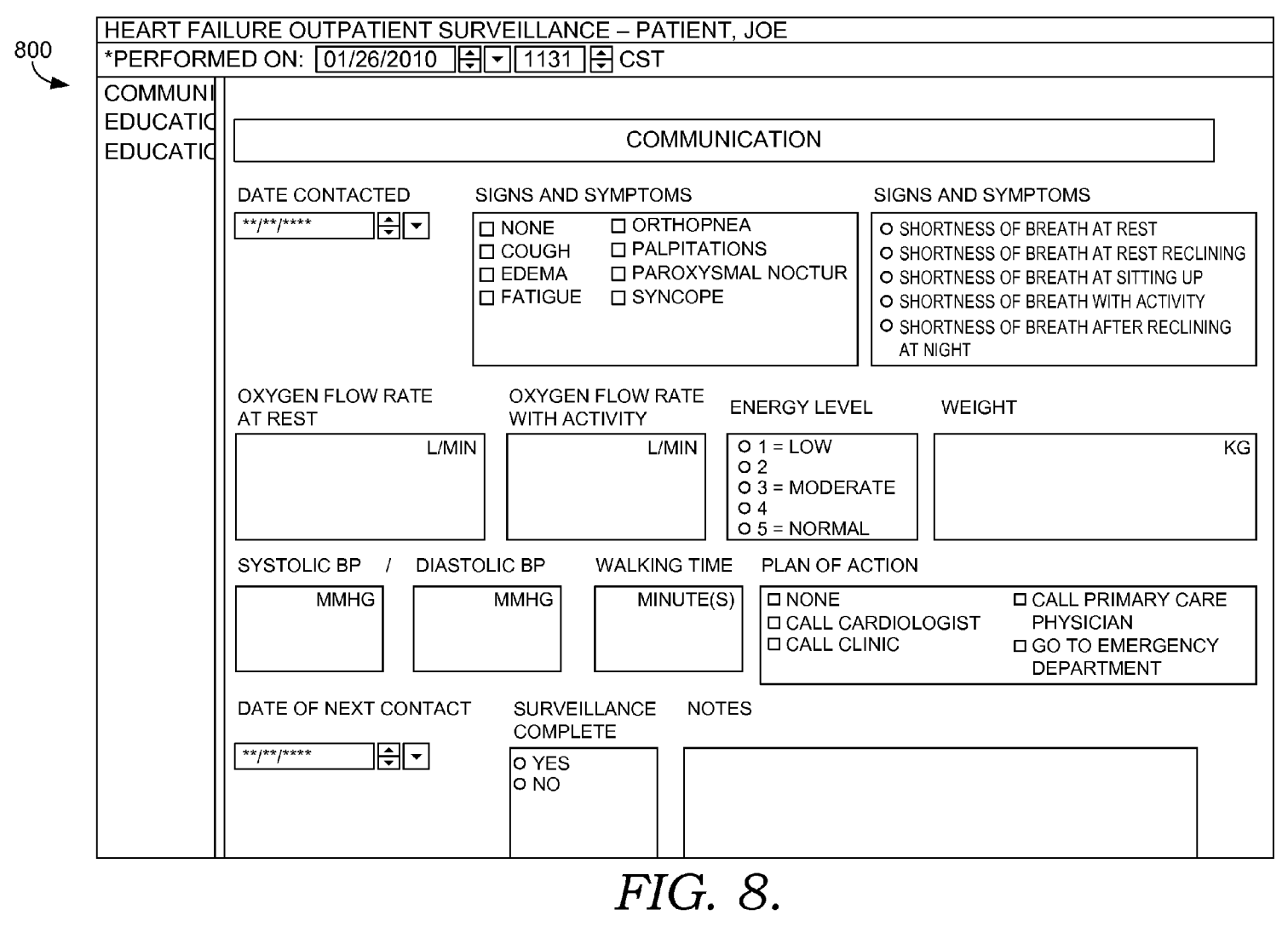

In some embodiments, the clinician may access patient information by selecting a patient from the call list. For instance, FIG. 7 illustrates patient information when "Joe Patient" is selected from the call list. The patient summary includes a readmission risk score for the patient providing the clinician with an indication of the readmission risk for the patient. The patient summary also includes a variety of information that may be useful to a clinician responsible for contacting the patient, including surveillance information from previous contacts, medications, problems, and other related documentation. Embodiments of the present invention may further provide user interfaces for collecting patient information when performing outpatient surveillance. FIG. 8 provides an illustrate screen display 800 of such a user interface. The user interface and the information to be collected may be triggered based upon the readmission risk for the patient.

As can be understood, the present invention provides a readmission risk prediction model built using linear regression techniques and clinically relevant data. The present invention further provides inpatient treatment interventions and outpatient activity recommendations based on patients' monitored readmission risk.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media storing computer-useable instructions that, when used by one or more computing devices, cause the one or more computing devices to perform a method comprising:

identifying a patient condition for a patient admitted to a clinical facility;

selecting, from a plurality of readmission risk prediction models, a readmission risk prediction model based on the patient condition, each readmission risk prediction model having been generated for a given condition using clinically relevant data from patients diagnosed with that given condition;

receiving a first set of patient data for the patient while the patient is admitted to the clinical facility;

computing a first readmission risk score using the readmission risk prediction model and the first set of patient data, the first readmission risk score representing a probability of readmission for the patient;

providing a first indication of readmission risk for the patient based on the readmission risk score for presentation to a clinician treating the patient;

providing an inpatient treatment recommendation for the patient based on the first readmission risk score;

receiving a second set of patient data for the patient after the patient has been discharged from the clinical facility;

computing a second readmission risk score using the readmission risk prediction model and the second set of patient data;

providing a second indication of readmission risk for the patient based on the second readmission risk score; and providing an outpatient treatment recommendation for the patient based on the second readmission risk score.

2. The one or more computer storage media of claim 1, wherein multiple patient conditions are identified for the patient, and wherein the readmission risk prediction model corresponds with the multiple patient conditions.

3. The one or more computer storage media of claim 1, wherein the method further comprises:

identifying a second patient condition for the patient; and selecting, from the plurality of readmission risk prediction models, a second readmission risk prediction model based on the second patient condition; and wherein the first readmission risk score is computed using the readmission risk prediction model, the second readmission risk prediction model, and the first set of patient data.

4. The one or more computer storage media of claim 1, wherein the first set of patient data is received from an electronic medical record.

5. The one or more computer storage media of claim 1, wherein the method further comprises:

determining that additional patient data is needed based on the readmission risk prediction model; and providing a notice for display to a clinician prompting the clinician to provide the additional patient data.

6. The one or more computer storage media of claim 1, wherein the method further comprises:

comparing the first readmission risk score against a readmission risk threshold; and determining the inpatient treatment recommendation based on comparison of the first readmission risk score against the readmission risk threshold.

7. The one or more computer storage media of claim 6, wherein the first readmission risk score is compared against a plurality of thresholds.

8. The one or more computer storage media of claim 6, wherein the patient is identified as a high readmission risk based on the first readmission risk score.

9. The one or more computer storage media of claim 1, wherein the inpatient treatment recommendation comprises one or more selected from the following: performing an alternate therapy, requesting an additional study to be performed on the patient, and extending the patient's length of stay.

10. The one or more computer storage media of claim 1, wherein the method further comprises computing a new readmission risk score while the patient is still admitted to the clinical facility and determining new inpatient treatment recommendations based on the new readmission risk score.

11. The one or more computer storage media of claim 1, wherein the method further comprises determining whether to discharge the patient based on the first readmission risk score.

12. The one or more computer storage media of claim 1, wherein the method further comprises performing discharge planning based on the first readmission risk score including determining one or more outpatient activities based on the first readmission risk score.

13. The one or more computer storage media of claim 1, wherein providing the outpatient treatment recommendation for the patient based on the second readmission risk score comprises comparing the second readmission risk score against one or more predetermined thresholds and determining the outpatient treatment recommendation based on the comparison.

14. The one or more computer storage media of claim 1, wherein providing the outpatient treatment recommendation for the patient based on the second readmission risk score comprises determining to readmit the patient based on the second readmission risk score.

15. The one or more computer storage media of claim 1, wherein the outpatient treatment recommendation comprises at least one selected from the following: performing outpatient monitoring, scheduling outpatient appointments for the patient, providing in-home healthcare, and educating the patient on healthcare issues related to the patient's condition.

16. The one or more computer storage media of claim 1, wherein providing the outpatient treatment recommendation based on the second readmission risk score comprises determining that the patient has a high risk for readmission based on the second readmission risk score and placing or maintaining the patient on a call list for high risk patients.

17. The one or more computer storage media of claim 1, wherein each readmission risk prediction model has been generated for a given condition based on a logistic regression model built using clinically relevant data from patients diagnosed with that given condition.

18. A method comprising:
 identifying, by a first computing process, a patient condition for a patient admitted to a clinical facility;
 selecting, by a second computing process, from a plurality of readmission risk prediction models, a readmission risk prediction model based on the patient condition, each readmission risk prediction model having been generated for a given condition using clinically relevant data from patients diagnosed with that given condition;
 receiving, by a third computing process, a first set of patient data for the patient while the patient is admitted to the clinical facility;
 computing, by a fourth computing process, a first readmission risk score using the readmission risk prediction model and the first set of patient data, the first readmission risk score representing a probability of readmission for the patient;
 providing, by a fifth computing process, a first indication of readmission risk for the patient based on the readmission risk score for presentation to a clinician treating the patient;
 providing, by a sixth computing process, an inpatient treatment recommendation for the patient based on the first readmission risk score;
 receiving, by a seventh computing process, a second set of patient data for the patient after the patient has been discharged from the clinical facility;
 computing, by an eight computing process, a second readmission risk score using the readmission risk prediction model and the second set of patient data;
 providing, by a ninth computing process, a second indication of readmission risk for the patient based on the second readmission risk score; and
 providing, by a tenth computing process, an outpatient treatment recommendation for the patient based on the second readmission risk score;
 wherein each of the computing processes is performed by one or more computing devices.

19. A computerized system comprising:
 one or more processors; and
 one or more computer storage media storing instructions that, when used by the one or more processors, cause the one or more processors to:
  identify a patient condition for a patient admitted to a clinical facility;
  select, from a plurality of readmission risk prediction models, a readmission risk prediction model based on the patient condition, each readmission risk prediction model having been generated for a given condition using clinically relevant data from patients diagnosed with that given condition;
  receive a first set of patient data for the patient while the patient is admitted to the clinical facility;
  compute a first readmission risk score using the readmission risk prediction model and the first set of patient data, the first readmission risk score representing a probability of readmission for the patient;
  provide a first indication of readmission risk for the patient based on the readmission risk score for presentation to a clinician treating the patient;
  provide an inpatient treatment recommendation for the patient based on the first readmission risk score;
  receive a second set of patient data for the patient after the patient has been discharged from the clinical facility;
  compute a second readmission risk score using the readmission risk prediction model and the second set of patient data;
  providing a second indication of readmission risk for the patient based on the second readmission risk score; and
  providing an outpatient treatment recommendation for the patient based on the second readmission risk score.

* * * * *